United States Patent [19]

Anderson

[11] Plant 4,079

[45] July 19, 1977

[54] DWARF NECTARINE TREE

[75] Inventor: Frederic W. Anderson, Merced, Calif.

[73] Assignee: Reedley Nursery, Inc., Reedley, Calif.

[21] Appl. No.: 717,862

[22] Filed: Aug. 25, 1976

[51] Int. Cl.[2] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A genetically dwarf nectarine tree, with short internodes, which is comparatively large, vigorous, upright, spreading, dense, foliated with large, lanceolate leaves having a glandular, crenate margin, blooms with large, pink flowers, and a regular and very productive bearer of large, uniform, symmetrical, globose, clingstone fruit having yellow skin substantially overspread with red, and yellow flesh.

1 Drawing Figure

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of dwarf nectarine tree resulted from my endeavors in the conduct of such plant breeding program.

ORIGIN OF THE VARIETY

The present variety of genetically dwarf nectarine tree was originated by me, in my experimental nursery and orchard located as aforesaid, as a cross between the Golden Prolific nectarine (U.S. Plant Pat. No. 2,193) as the seed parent, and Early Sun Grand (U.S. Plant Pat. No. 1,420) as the pollen parent. The variety, as thus originated, and under careful and continuing observation, evidenced — upon bearing fruit — certain novel characteristics which were commercially desirable, and I, therefore, undertook asexual reproduction of the variety preparatory to introducing it to the trade.

ASEXUAL REPRODUCTION OF THE VARIETY

Subsequent to origination and selection by me of the present variety of nectarine tree, in the manner above described, I asexually reproduced it by top-working on mature peach trees in my said experimental orchard, and — in maturity — such reproductions ran true to the original tree in all respects.

SUMMARY OF THE VARIETY

The herein claimed new and distinct variety of genetically dwarf nectarine tree, which has short internodes, is comparatively large, vigorous, upright, spreading, dense, foliated with large, lanceolate leaves having a glandular, crenate margin, blooms with large, pink flowers, and a regular and very productive bearer of large, uniform, symmetrical, globose, clingstone fruit having yellow skin substantially overspread with red, and yellow flesh; the tree of the present variety, because of such short internodes, being only about 30 percent as high as the Red Grand nectarine (U.S. Plant Pat. No. 1,060), although the fruit of the present variety, in size and appearance, resembles that of said Red Grand nectarine but with much less red around the pit. By reason of such lesser height of the tree, thinning thereof, and harvesting of the fruit, can be accomplished more economically and with greater ease.

BRIEF DESCRIPTION OF THE DRAWING

The drawing is an illustration, by photographic reproduction in color, of a twig with leaves, and fruit of the variety; one of the latter being partially cut away to expose the flesh.

DESCRIPTION OF THE VARIETY

The botanical details of this new and distinct variety of dwarf nectarine tree — with color definitions (except those in common color terms) referenced to Maerz and Paul Dictionary of Color — are as follows:

Tree:
- *Class.*—Genetically dwarf, with short internodes.
- *Size.*—Large, as compared to other dwarf nectarine trees.
- *Vigor.*—Vigorous.
- *Growth.*—Upright — spreading.
- *Density*—Dense.
- *Production.*—Productive to very productive.
- *Bearing.*—Regular bearer.

Trunk:
- *Size.*—Medium.

Branches:
- *Size.*—Stocky.

Leaves:
- *Size.*—Large; average length — 9"; Average width — $1\frac{3}{8}$".
- *Form.*—Lanceolate; acutely pointed.
- *Thickness.*—Medium.
- *Margin.*—Glandular; crenate.
- *Petiole.*—Average number and position — 2 to 3 on petiole; usually 2 on blade; alternate; reniform.
- *Color.*—Top side — Medium green (23-L-9); under side — Lighter green (22-J-6).

Flowers:
- *Blooming period.*—Date of first bloom — Mar. 4, 1976. Date of full bloom — Mar. 13, 1976. Medium, as compared with other varieties.
- *Size.*—Large.
- *Color.*—Pink.

Fruit:

*Maturity when described.*—Eating ripe — July 30, 1976.

*Date of first picking.*—July 15, 1976.

*Date of last picking.*—July 25, 1976.

*Size.*—Large; uniform; average diameter axially — 2½"; average transversely in suture plane — 2½".

*Form.*—Uniform; symmetrical; globose.

*Suture.*—Distinct; shallow; extends from base to apex, with slight depression beyond pistil point.

*Ventral surface.*—Rounded.

*Cavity.*—Rounded; elongated in suture plane.

*Base.*—Rounded.

*Apex.*—Short; depressed.

*Pistil point.*—Inconspicuous.

Skin:

*Thickness.*—Medium.

*Texture.*—Medium.

*Tenacity.*—Tenacious to flesh.

*Tendency to crack.*—None noted.

*Down.*—Wanting.

*Color.*—Yellow (9-L-7) substantially overspread with red (5-L-5 to 7-L-5) with yellow speckling and red mottling.

Flesh:

*Texture.*—Firm; fine; crisp; meaty; melting.

*Ripens.*—Evenly.

*Flavor.*—Subacid; Vinous.

*Eating quality.*—Fair to good.

*Color.*—Yellow (9-L-6) lightly streaked with red.

Stone:

*Type.*—Cling; adheres to flesh over entire surface.

*Size.*—Large; average length — 1½"; average breadth — 1"; average thickness — ¾".

*Form.*—Oblong to oval.

*Base.*—Straight.

*Apex.*—Rounded.

*Sides.*—Equal.

*Tendency to split.*—Slight.

*Color.*—Red (7-L-6).

Use: Market — local. Long distance shipping.

Keeping quality: Medium.

Resistance to insects and diseases: No unusual susceptibilities noted.

Shipping quality: Medium.

The dwarf nectarine tree and its fruit herein described may vary in slight detail due to climatic and soil conditions under which the variety may be grown; the present description being of the variety as grown in the Central Valley of Calif.

I claim:

1. A new and distinct variety of genetically dwarf nectarine tree, substantially as illustrated and described, which has short internodes, is comparatively large, vigorous, upright, spreading, dense, foliated with large, lanceolate leaves having a glandular, crenate margin, blooms with large, pink flowers, and a regular and very productive bearer of large, uniform, symmetrical, globose, clingstone fruit having yellow skin substantially overspread with red, and yellow flesh; the tree, because of such short internodes, being only about 30 percent as high as the Red Grand nectarine, although the fruit, in size and appearance, resembles that of the latter but with much less red around the pit.

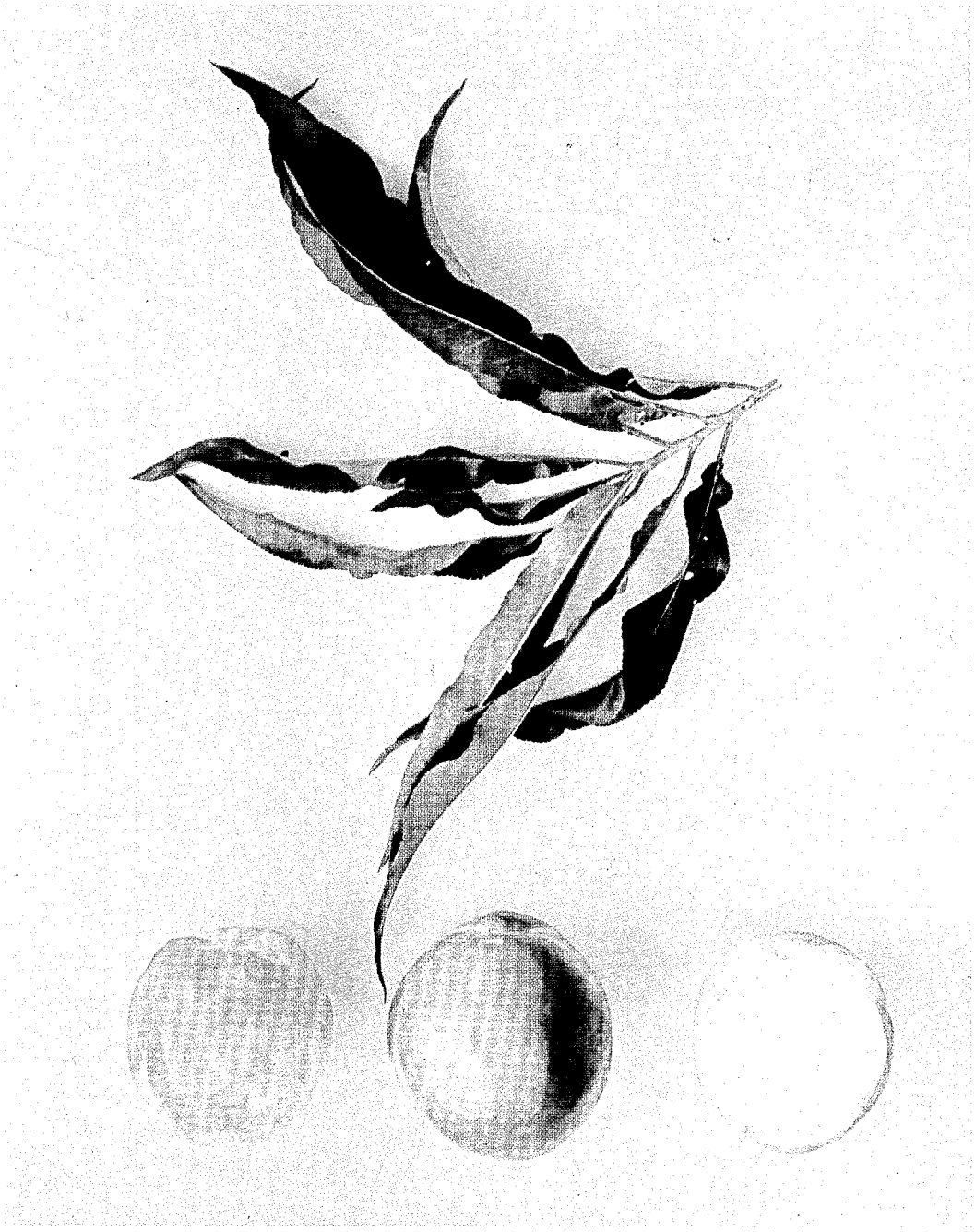

* * * * *